United States Patent [19]
Khouri et al.

[11] Patent Number: 6,110,482
[45] Date of Patent: *Aug. 29, 2000

[54] MANUFACTURE OF AUTOGENOUS REPLACEMENT BODY PARTS

[75] Inventors: Roger K. Khouri, St. Louis, Mich.; Kuber T. Sampath, Medway; David C. Rueger, Hopkinton, both of Mass.

[73] Assignee: Styker Corporation, Kalamazoo, Mich.

[ * ] Notice: This patent is subject to a terminal disclaimer.

[21] Appl. No.: 08/459,129

[22] Filed: Jun. 2, 1995

Related U.S. Application Data

[63] Continuation-in-part of application No. 08/253,398, Jun. 3, 1994, Pat. No. 5,906,827.

[51] Int. Cl.$^7$ .............................. A61F 2/02; A61F 2/04; A61F 2/28; A61F 2/30
[52] U.S. Cl. .......................... 424/423; 424/491; 623/11; 623/12; 623/16; 623/18; 623/20
[58] Field of Search ................................ 623/11, 12, 16, 623/18, 20; 424/423, 484, 491

[56] References Cited

U.S. PATENT DOCUMENTS

| | | |
|---|---|---|
| 4,385,404 | 5/1983 | Sully et al. . |
| 4,877,864 | 10/1989 | Wang et al. . |
| 4,880,429 | 11/1989 | Stone . |
| 4,968,590 | 11/1990 | Kuberasampath et al. . |
| 4,975,526 | 12/1990 | Kuberasampath et al. . |
| 5,011,691 | 4/1991 | Oppermann et al. . |
| 5,013,649 | 5/1991 | Wang et al. . |
| 5,041,138 | 8/1991 | Vacanti et al. . |
| 5,061,286 | 10/1991 | Lyle . |
| 5,067,940 | 11/1991 | Liboff et al. . |
| 5,067,962 | 11/1991 | Campbell et al. ........................ 623/13 |
| 5,067,963 | 11/1991 | Khouri . |
| 5,067,964 | 11/1991 | Richmond et al. . |
| 5,108,753 | 4/1992 | Kuberasampath et al. . |
| 5,116,738 | 5/1992 | Wang et al. . |
| 5,154,189 | 10/1992 | Oberlander . |
| 5,171,574 | 12/1992 | Kuberasampath et al. . |
| 5,190,547 | 3/1993 | Barber, Jr. et al. ........................ 606/79 |
| 5,206,023 | 4/1993 | Hunziker . |
| 5,258,494 | 11/1993 | Oppermann et al. . |
| 5,266,683 | 11/1993 | Oppermann et al. . |
| 5,270,300 | 12/1993 | Hunziker . |
| 5,326,357 | 7/1994 | Kandel . |
| 5,344,654 | 9/1994 | Rueger et al. . |
| 5,354,557 | 10/1994 | Oppermann et al. . |
| 5,413,989 | 5/1995 | Ogawa et al. ............................ 514/12 |
| 5,430,019 | 7/1995 | Rogers et al. ............................ 514/12 |
| 5,492,697 | 2/1996 | Boyan et al. ............................ 424/422 |
| 5,658,882 | 8/1997 | Celeste et al. ............................ 514/12 |
| 5,846,931 | 12/1998 | Hattersley et al. ........................ 514/2 |
| 6,020,313 | 12/1999 | Clarke et al. ............................ 514/21 |

FOREIGN PATENT DOCUMENTS

| | | |
|---|---|---|
| 0206801 | 6/1986 | European Pat. Off. . |
| 0567391A1 | 4/1993 | European Pat. Off. . |
| WO88/00205 | 1/1988 | WIPO . |
| WO89/09788 | 10/1989 | WIPO . |
| WO91/11366 | 10/1990 | WIPO . |
| WO 91/05802 | 5/1991 | WIPO . |
| WO91/18098 | 11/1991 | WIPO . |
| WO91/18558 | 12/1991 | WIPO . |
| WO93/00432 | 1/1993 | WIPO . |
| WO 93/25246 | 12/1993 | WIPO . |
| WO95/01131 | 6/1994 | WIPO . |
| WO94/26892 | 11/1994 | WIPO . |
| WO94/26893 | 11/1994 | WIPO . |
| WO 95/16035 | 6/1995 | WIPO . |
| WO95/16035 | 6/1995 | WIPO . |
| WO 96/36710 | 11/1996 | WIPO . |
| WO 96/39169 | 12/1996 | WIPO . |

OTHER PUBLICATIONS

Okada et al. "Experimental Studies on half–joint transplantation", International Orthopaedics (1990) 14(3) 261–7.
Johnson et al. "Repair of Segmental Defects of the Tibia . . . ", Clin. Orthop. 1988; 236: 249–257.
Urist "Surface—Decalcified Allogenic Bone (SDAB) Implants", Clin. Orthop. 1968; 56: 37–50.
Johnson et al. "Resistant Nonunions and Partial or Complete Segmental Defects of Long Bones", Clin. Orthop. 1992;277: 229–37.
Gresham, "The Freeze–dried Cortical Bone Homograft . . . ", Clinical Orthopaedics and Related Research, 37, p. 194–200 (1964).
Urist et al. "A Chemosterilized . . . Alloimplant for Bone Banks" Archives of Surgery, vol. 110, No. 4, p. 416–428 (1975).
Prolo et al. "Ethylene Oxide Sterilization of Bone . . . ", Neurosurgery, vol. 6, No. 5, p. 529–539 (May 1980).
Carr et al. "Clinical Evaluation of Freeze–Dried Bone Grafts", Journal of Bone and Joint Surgery, p. 549–614 (1955).
Sampath et al. (1983), "Homology of Bone–Inductive Proteins From Human, Monkey, Bovine, and Rat Extracellular Matrix," Proc. Natl. Acad. Sci. USA 80:6591–6595.
Padgett et al. (1987), "A Transcript from a Drosophila Pattern Gene Predicts a Protein Homologous to the Transforming Growth Factor–B Family," Nature 325:81–84.
Sampath et al. (1987), "Dissociative Extraction and Reconstitution of Extracellular Matrix Components Involved In Local Bone Differentiation," Proc. Natl. Acad. Sci. USA 78:7599–7603.
Weeks (1987) "Maternal mRNA Localized to the Vegetal Hemisphere Xenopus Eggs Codes for a Growth Factor Related to TGF–B," Cell 51:861–867.
Wozney et al. (1988), "Novel Regulators of Bone Formation: Molecular Clones and Activities," Science 24:1528–1533.
Lyons et al. (1989), "VGR–1, A Mammalian Gene Related to Xenopus VG–1, is a member of the Transforming Growth Factor Beta Gene Superfamily," Proc. Natl. Acad. Sci. USA 4554–4558.

(List continued on next page.)

Primary Examiner—Jeffrey C. Mullis
Attorney, Agent, or Firm—Testa, Hurwitz & Thibeault, LLP

[57] ABSTRACT

Disclosed are matrix materials, methods, and devices for manufacture in vivo of autogenous replacement body parts comprising plural distinct tissues. In one embodiment, the replacement body part is a skeletal joint and the new plural distinct tissues include bone and articular cartilage.

30 Claims, 3 Drawing Sheets

OTHER PUBLICATIONS

Celeste et al. (1990), "Identification of Transforming Growth Factor Beta Family Members Present in Bone–Inductive Protein Purified from Bovine Bone," *Proc. Natl. Acad. Sci. USA* 87:9843–9847.

Ozkaynak et al. (1990), "OP–1 cDNA Encodes an Osteogenic Protein in the TGF–B Family," *Embo J.* 9:2085–2093.

Sampath et al. (1990), "Bovine Osteogenic Protein Is Composed of Dimers of OP–1 and BMP–2A, Two Members of the Transforming Growth FActor–B Superfamily," *J. Biol. Chem.* 265:13198–13205.

Wharton et al. (1991), "Drosophila 60A Gene, Another Transforming Growth Factor β Family Member, is Closely Related to Human Bone Morphogenetic Proteins," *Proc. Natl. Acad. Sci. USA* 88:9214–9218.

Ozkaynak et al. (1992), "Osteogenic Protein–2," *J. Biol. Chem.* 267:25220–25227.

Sampath et al. (1993), "Drosophila Transforming Growth Factor B Superfamily Proteins Induce Endochondral Bone Formation in Mammals," *Proc. Natl. Acad. Sci. USA* 90:6004–6008.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 1822 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: HOMO SAPIENS
       (F) TISSUE TYPE: HIPPOCAMPUS (ix) FEATURE:
       (A) NAME/KEY: CDS
       (B) LOCATION: 49..1341
       (C) IDENTIFICATION METHOD: experimental
       (D) OTHER INFORMATION: /function= "OSTEOGENIC PROTEIN"
          /product= "OP1"
          /evidence= EXPERIMENTAL
          /standard_name= "OP1"

(xi) SEQUENCE DESCRIPTION: SEQ ID NO:1:

```
GGTGCGGGCC CGGAGCCCGG AGCCCGGGTA GCGCGTAGAG CCGGCGCG ATG CAC GTG        57
                                                   Met His Val
                                                     1

CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
      5              10                  15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
 20              25                  30                  35

GAG GTG CAC TCG AGC TTC ATC CAC CGG GCG CTC CGC AGC CAG GAG CGG        201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC        249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG        297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC        345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC        393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
                 120                 125                 130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
             135                 140                 145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
```

```
                150                      155                     160
CCA GAA GGG GAA GCT GTC ACG GCA GCC GAA TTC CGG ATC TAC AAG GAC       585
Pro Glu Gly Glu Ala Val Thr Ala Ala Glu Phe Arg Ile Tyr Lys Asp
    165                     170                     175

TAC ATC CGG GAA CGC TTC GAC AAT GAG ACG TTC CGG ATC AGC GTT TAT       633
Tyr Ile Arg Glu Arg Phe Asp Asn Glu Thr Phe Arg Ile Ser Val Tyr
180                     185                     190                 195

CAG GTG CTC CAG GAG CAC TTG GGC AGG GAA TCG GAT CTC TTC CTG CTC       681
Gln Val Leu Gln Glu His Leu Gly Arg Glu Ser Asp Leu Phe Leu Leu
                    200                     205                 210

GAC AGC CGT ACC CTC TGG GCC TCG GAG GAG GGC TGG CTG GTG TTT GAC       729
Asp Ser Arg Thr Leu Trp Ala Ser Glu Glu Gly Trp Leu Val Phe Asp
                215                     220                     225

ATC ACA GCC ACC AGC AAC CAC TGG GTG GTC AAT CCG CGG CAC AAC CTG       777
Ile Thr Ala Thr Ser Asn His Trp Val Val Asn Pro Arg His Asn Leu
            230                     235                     240

GGC CTG CAG CTC TCG GTG GAG ACG CTG GAT GGG CAG AGC ATC AAC CCC       825
Gly Leu Gln Leu Ser Val Glu Thr Leu Asp Gly Gln Ser Ile Asn Pro
        245                     250                     255

AAG TTG GCG GGC CTG ATT GGG CGG CAC GGG CCC CAG AAC AAG CAG CCC       873
Lys Leu Ala Gly Leu Ile Gly Arg His Gly Pro Gln Asn Lys Gln Pro
260                     265                     270                 275

TTC ATG GTG GCT TTC TTC AAG GCC ACG GAG GTC CAC TTC CGC AGC ATC       921
Phe Met Val Ala Phe Phe Lys Ala Thr Glu Val His Phe Arg Ser Ile
                    280                     285                 290

CGG TCC ACG GGG AGC AAA CAG CGC AGC CAG AAC CGC TCC AAG ACG CCC       969
Arg Ser Thr Gly Ser Lys Gln Arg Ser Gln Asn Arg Ser Lys Thr Pro
                295                     300                     305

AAG AAC CAG GAA GCC CTG CGG ATG GCC AAC GTG GCA GAG AAC AGC AGC      1017
Lys Asn Gln Glu Ala Leu Arg Met Ala Asn Val Ala Glu Asn Ser Ser
            310                     315                     320

AGC GAC CAG AGG CAG GCC TGT AAG AAG CAC GAG CTG TAT GTC AGC TTC      1065
Ser Asp Gln Arg Gln Ala Cys Lys Lys His Glu Leu Tyr Val Ser Phe
        325                     330                     335

CGA GAC CTG GGC TGG CAG GAC TGG ATC ATC GCG CCT GAA GGC TAC GCC      1113
Arg Asp Leu Gly Trp Gln Asp Trp Ile Ile Ala Pro Glu Gly Tyr Ala
340                     345                     350                 355

GCC TAC TAC TGT GAG GGG GAG TGT GCC TTC CCT CTG AAC TCC TAC ATG      1161
Ala Tyr Tyr Cys Glu Gly Glu Cys Ala Phe Pro Leu Asn Ser Tyr Met
                    360                     365                 370

AAC GCC ACC AAC CAC GCC ATC GTG CAG ACG CTG GTC CAC TTC ATC AAC      1209
Asn Ala Thr Asn His Ala Ile Val Gln Thr Leu Val His Phe Ile Asn
                375                     380                     385

CCG GAA ACG GTG CCC AAG CCC TGC TGT GCG CCC ACG CAG CTC AAT GCC      1257
Pro Glu Thr Val Pro Lys Pro Cys Cys Ala Pro Thr Gln Leu Asn Ala
            390                     395                     400

ATC TCC GTC CTC TAC TTC GAT GAC AGC TCC AAC GTC ATC CTG AAG AAA      1305
Ile Ser Val Leu Tyr Phe Asp Asp Ser Ser Asn Val Ile Leu Lys Lys
        405                     410                     415

TAC AGA AAC ATG GTG GTC CGG GCC TGT GGC TGC CAC TAGCTCCTCC           1351
Tyr Arg Asn Met Val Val Arg Ala Cys Gly Cys His
420                     425                     430

GAGAATTCAG ACCCTTTGGG GCCAAGTTTT TCTGGATCCT CCATTGCTCG CCTTGGCCAG    1411

GAACCAGCAG ACCAACTGCC TTTTGTGAGA CCTTCCCCTC CCTATCCCCA ACTTTAAAGG    1471

TGTGAGAGTA TTAGGAAACA TGAGCAGCAT ATGGCTTTTG ATCAGTTTTT CAGTGGCAGC    1531

ATCCAATGAA CAAGATCCTA CAAGCTGTGC AGGCAAAACC TAGCAGGAAA AAAAAACAAC    1591

GCATAAAGAA AAATGGCCGG GCCAGGTCAT TGGCTGGGAA GTCTCAGCCA TGCACGGACT    1651
```

```
CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAAATTGAC CCGGAAGTTC    1771

CTGTAATAAA TGTCACAATA AAACGAATGA ATGAAAAAAA AAAAAAAAAA A            1822
```

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
             85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320
```

-continued

```
Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

(2) INFORMATION FOR SEQ ID NO:3:

(i) SEQUENCE CHARACTERISTICS:
          (A) LENGTH: 102 amino acids
          (B) TYPE: amino acid
          (D) TOPOLOGY: linear (ii) MOLECULE TYPE: protein (ix) FEATURE:
          (A) NAME/KEY: Protein
          (B) LOCATION: 1..102
          (D) OTHER INFORMATION: /label= OPX
               /note= "WHEREIN EACH XAA IS INDEPENDENTLY SELECTED
               FROM A GROUP OF ONE OR MORE SPECIFIED AMINO ACIDS
               AS DEFINED IN THE SPECIFICATION"

(xi) SEQUENCE DESCRIPTION: SEQ ID NO:3:

Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

MANUFACTURE OF AUTOGENOUS REPLACEMENT BODY PARTS

RELATION TO RELATED APPLICATIONS

This application is a continuation-in-part of U.S. Ser. No. 08/253,398, filed Jun. 3, 1994, now U.S. Pat. No. 5,906,827 the disclosure of which is incorporated herein by reference.

FIELD OF THE INVENTION

This invention relates to materials and methods for the repair and regeneration of plural distinct tissues at a single defect site in a mammal. More particularly, the invention is concerned with materials and methods for the manufacture in vivo of autogenous replacement body parts, including mammalian skeletal joints, comprising plural different tissues, such as ligament, articular cartilage and bone tissues.

BACKGROUND OF THE INVENTION

Skeletal joints provide a movable union of two or more bones. Synovial joints are highly evolved articulating joints that permit free movement. Because mammalian lower limbs are concerned with locomotion and upper limbs provide versatility of movement, most of the joints in the extremities are of the synovial type. There are various types of synovial joints. Their classification is based upon the types of active motion that they permit (uniaxial, biaxial, and polyaxial). They are differentiated further according to their principal morphological features (hinge, pivot, condyloid). In contrast to fibrous and cartilaginous joints where the ends of the bones are found in continuity with intervening tissue, the ends of the bones in a synovial joint are in contact, but separate. Because the bones are not bound internally, the integrity of a synovial joint results from its ligaments and capsule (which bind the articulation externally) and to some extent from the surrounding muscles. In synovial joints, the contiguous bony surfaces are covered with articular or, hyaline cartilage, and the joint cavity is surrounded by a fibrous capsule which segregates the joint from the surrounding vascularized environment. The inner surface of the capsule is lined by a synovial layer or "membrane" containing cells involved in secreting the viscous lubricating synovial fluid. Gray, *Anatomy of the Human Body*, pp. 312; 333–336 (13th ed.; C. C. Clemente, ed., (1985)).

In certain synovial joints, the joint or synovial cavity may be divided by a meniscus of fibrocartilage. Synovial joints involving two bones and containing a single joint cavity are referred to as simple joints. Joints that contain a meniscus forming two joint cavities are called composite joints. The term compound joint is used for those articulations in which more than a single pair of articulating surfaces are present.

Joint replacement, particularly articulating joint replacement, is a commonly performed procedure in orthopedic surgery. However, the ideal material for replacement joints remains elusive. Typically, joint reconstruction requires repair of the bony detect, the articular cartilage and, in addition, one or more of the joining ligaments. To date, there are no satisfactory clinical means for readily repairing both articular cartilage and bony defects within a joint which reliably results in viable, fully-functional weight-bearing joints. Prosthetic joints which replace all the endogenous joint tissues circumvent some of these problems. However, prosthetic joints have numerous, well documented limitations, particularly in younger and highly active patients. In addition, in some circumstances prosthetic joint replacement is not possible and repair options are limited to osteochondroallograft materials.

The articular, or hyaline cartilage, found at the end of articulating bones is a specialized, histologically distinct tissue and is responsible for the distribution of load resistance to compressive forces, and the smooth gliding that is part of joint function. Articular cartilage has little or no self-regenerative properties. Thus, if the articular cartilage is torn or worn down in thickness or is otherwise damaged as a function of time, disease or trauma, its ability to protect the underlying bone surface is compromised.

Other types of cartilage in skeletal joints include fibrocartilage and elastic cartilage. Secondary cartilaginous joints are formed by discs of fibrocartilage which join vertebrae in the vertebral column. In fibrocartilage, the mucopolysaccharide network is interlaced with prominent collagen bundles and the chondrocytes are more widely scattered than in hyaline cartilage. Elastic cartilage contains collagen fibers which are histologically similar to elastin fibers. As with other connective tissues the formation of cartilaginous tissue is a complex biological process, involving the interaction of cells and collagen fibers in a unique biochemical milieu.

Cartilage tissue, including articular cartilage, unlike other connective tissues, lacks blood vessels, nerves, lymphatics and basement membrane. Cartilage is composed of chondrocytes which synthesize an abundant extracellular milieu composed of water, collagens, proteoglycans and noncollagenous proteins and lipids. Collagen serves to trap proteoglycans and to provide tensile strength to the tissue. Type II collagen is the predominant collagen in cartilage tissue. The proteoglycans are composed of a variable number of glycosaminoglycan chains, keratin sulphate, chondroitin sulphate and/or dermatan sulphate, and N-linked and O-linked oligosaccharides covalently bound to a protein core. The sulfated glycosaminoglycans are negatively charged resulting in an osmotic swelling pressure that draws in water.

In contrast, certain collagens such as the fibrotic cartilaginous tissues which occur in scar tissue for example, are keloid and typical of scar-type tissue, i.e., composed of capillaries and abundant, irregular, disorganized bundles of Type I and Type II collagen.

Histologically, articular or hyaline cartilage can be distinguished from other forms of cartilage, both by its morphology and by its biochemistry. Morphologically, articular cartilage is characterized by superficial versus mid versus deep "zones" which show a characteristic gradation of features from the surface of the tissue to the base of the tissue adjacent to the bone. In the superficial zone, for example, chondrocytes are flattened and lie parallel to the surface embedded in an extracellular network that contains tangentially arranged collagen and few proteoglycans. In the mid zone, chondrocytes are spherical and surrounded by an extracellular network rich in proteoglycans and obliquely organized collagen fibers. In the deep zone, close to the bone, the collage fibers are vertically oriented. The keratin sulphate rich proteoglycans increase in concentration with increasing distance from the cartilage surface. For a detailed description of articular cartilage micro-structure, see, for example, (Aydelotte and Kuettner, (1988), *Conn. Tiss. Res.* 18:205; Zanetti et al., (1985), *J. Cell Biol.* 101:53; and Poole et al., (1984), *J. Anat.* 138:13.

Biochemically, articular collagen can be identified by the presence of Type II and Type IX collagen, as well as by the presence of well-characterized proteoglycans, and by the absence of Type X collagen, which is associated with endochondral bone formation.

In normal articular cartilage, a balance exists between synthesis and destruction of the above-described extracellular network. However, in tissue subjected to repeated trauma, for example due to friction between misaligned bones in contact with one another, or in joint diseases characterized by net loss of articular cartilage, e.g., osteoarthritis, an imbalance occurs between synthesis and degradation.

Two types of defects are recognized in articular surfaces, i.e., full-thickness defects and superficial defects. These defects differ not only in the extent of physical damage to the cartilage, but also in the nature of the repair response each type of lesion can elicit.

Full-thickness defects of an articulating surface include damage to the hyaline cartilage, the calcified cartilage layer and the subchondral bone tissue with its blood vessels and bone marrow. Full-thickness defects can cause severe pain since the bone plate contains sensory nerve endings. Such defects generally arise from severe trauma and\or during the late stages of degenerative joint disease, such as osteoarthritis. Full-thickness defects may, on occasion, lead to bleeding and the induction of a repair reaction from the subchondral bone. In such instances, however, the repair tissue formed is a vascularized fibrous type of cartilage with insufficient biomechanical properties, and does not persist on a long-term basis.

In contrast, superficial defects in the articular cartilage tissue are restricted to the cartilage tissue itself. Such defects are notorious because they do not heal and show no propensity for repair reactions. Superficial defects may appear as fissures, divots, or clefts in the surface of the cartilage, or they may have a "crab-meat" appearance in the affected tissue. They contain no bleeding vessels (blood spots) such as are seen in full-thickness defects. Superficial defects may have no known cause, however, they are often the result of mechanical derangements which lead to a wearing down of the cartilaginous tissue. Such mechanical derangements may be caused by trauma to the joint, e.g., a displacement of torn meniscus tissue into the joint, meniscectomy, a taxation of the joint by a torn ligament, malalignment of joints, or bone fracture, or by hereditary diseases. Superficial defects are also characteristic of early stages of degenerative joint diseases, such as osteoarthritis. Since the cartilage tissue is not innervated or vascularized, superficial defects do not heal and often degenerate into full-thickness defects.

Replacement with prosthetic joints is currently the preferred option for serious degeneration of joint function involving loss of articular cartilage. It is anticipated that a means for functional reconstruction of joint complexes, including regeneration and repair of articular cartilage, will have a profound effect on alloplastic joint replacement surgery and the management of degenerative joint disease.

Like articular cartilage, joint ligaments which serve to connect interacting bones in the joint, have little or no self-regenerative properties. Ligaments typically are composed of substantially parallel bundles of white fibrous tissue. They are pliant and flexible to allow substantially complete freedom of movement, but are inextensile to prevent over-extension of the interacting bones in the joint. Like cartilage, ligament tissue is substantially devoid of blood vessels and has little or no self-regenerative properties. Surgical repair of torn or damaged ligament tissue to date is limited to use of autogenous grafts or synthetic materials that are surgically attached to the articular extremities of the bones. Allogenic ligaments typically fail mechanically, presumably due to the treatments required to render these materials biocompatible. Similarly, tendons are rope-like structures which connect muscle fibers to bone or cartilage and which are formed from substantially parallel fibroids of white connective tissue. The synovial capsule is composed of a thin layer of ligamentous tissue which encloses the joint and allows the joint to be bathed in the lubricating synovial fluid. The interior of the joint capsule is lined with a thin membrane of connective tissue having branched connective-tissue corpuscles defining the synovial membrane, and which is primarily responsible for secreting synovial fluid into the cavity. The integrity of this membrane therefore, is important to maintaining a source for the lubricating synovial fluid. Repair of these tissues in orthopedic contexts typically is limited to resuturing of existing tissue.

Bone tissue differs significantly from the other tissues described hereinabove, including cartilage tissue. Specifically, bone tissue is vascularized tissue composed both of cells and a biphasic medium which is composed of a mineralized, inorganic component (primarily hydroxyapatite crystals) and an organic component comprised primarily of Type I collagen. Glycosaminoglycans constitute less than 2% of this organic component and less than 1% of the biphasic medium itself or of bone tissue per se. Moreover, relative to cartilage tissue, the collagen present in bone tissue exists in a highly-organized parallel arrangement.

Bony defects, whether from degenerative, traumatic or cancerous etiologies, pose a formidable challenge to the reconstructive surgeon. Particularly difficult is reconstruction or repair of skeletal parts that comprise part of a multi-tissue complex, such as occurs in mammalian joints.

Mammalian bone tissue is known to contain one or more proteinaceous materials presumably active during growth and natural bone healing which can induce a developmental cascade of cellular events resulting in endochondral bone formation. The developmental cascade involved in endochondral bone differentiation consists of chemotaxis of mesenchymal cells, proliferation of progenitor cells into chondrocytes and osteoblasts, differentiation of cartilage, vascular invasion, bone formation, remodeling, and finally marrow differentiation.

True osteogenic factors capable of inducing the above-described cascade of events that result in endochondral bone formation have now been identified, isolated, and cloned. These proteins, which occur in nature as disulfide-bonded dimeric proteins, are referred to in the art as "osteogenic" proteins, "osteoinductive" proteins, and "bone morphogenetic" proteins. Whether naturally-occurring or synthetically prepared, these osteogenic proteins, when implanted in a mammal typically in association with a substrate that allows the attachment, proliferation and differentiation of migratory progenitor cells, are capable of inducing recruitment of accessible progenitor cells and stimulating their proliferation, inducing differentiation into chondrocytes and osteoblasts, and further inducing differentiation of intermediate cartilage, vascularization, bone formation, remodeling, and finally marrow differentiation. Those proteins are referred to as members of the Vgr-1/OP1 protein subfamily of the TGFβ super gene family of structurally related proteins. Members include the proteins described in the art as OP1 (BMP-7), OP2 (BMP-8), BMP2, BMP3, BMP4, BMP5, BMP6, 60A, DPP, Vgr-1 and Vgl. See., e.g., U.S. Pat. No. 5,011,691; U.S. Pat. No. 5,266,683, Ozkaynak et al. (1990) *EMBO J.* 9: 2085–2093, Wharton et al. (1991) *PNAS* 88:9214–9218), (Ozkaynak (1992) *J. Biol. Chem.*

267:25220–25227 and U.S. Pat. No. 5,266,683); (Celeste et al. (1991) *PNAS* 87:9843–9847); (Lyons et al. (1989) *PNAS* 86:4554–4558). These disclosures describe the amino acid and DNA sequences, as well as the chemical and physical characteristics of these proteins. See also (Wozney et al. (1988) *Science* 242:1528–1534); BMP 9 (WO93/00432, published Jan. 7, 1993); DPP (Padgett et al. (1987) *Nature* 325:81–84; and Vg-1 (Weeks (1987) *Cell* 51:861–867).

It is an object of the instant invention to provide a bioresorbable matrix and device, suitable for regenerating body parts which comprise two or more functionally- and structurally-associated yet distinct replacement tissues in a mammal. Another object is to provide compositions and methods for the repair or complete reconstruction of a mechanically and functionally viable skeletal joint in a mammal, particularly an articulating or synovial joint, as well as other body parts comprising bone and bona fide hyaline cartilage, without relying on prosthetic devices. Another object is to provide materials and methods for the repair of tissue defects in an articulating mammalian joint, so as to form a mechanically and functionally viable joint comprising bone and articular cartilage, ligament, tendon, synovial membrane and synovial capsule tissue. Another object of the invention is to provide means for restoring functional non-mineralized tissue in a skeletal joint including the avascular tissue therein.

SUMMARY OF THE INVENTION

In accordance with the present invention, methods and devices are provided for the manufacture of a live autogenous replacement part comprising plural distinct tissues. In one aspect the replacement body part includes part or all of a mammalian skeletal joint, including an articulating or synovial joint. As described herein below, the methods and compositions of the invention are sufficient to restore mechanical and functional viable of the tissues associated with a skeletal joint, including bone (and bone marrow), articular cartilage, ligament, tendon, synovial capsule and synovial membrane tissues. Thus the invention provides methods and compositions for replacement of one or more of the plural distinct tissues that define a mammalian skeletal joint.

The invention provides, in one aspect therefore, a novel matrix for forming a mechanically and structurally functional, mammalian, replacement body part comprising plural distinct tissues. The matrix comprises intact residues specific for or characteristic of, and/or derived from at least two distinct tissues of the replacement body part. As will be appreciated from the description provided herein below, the matrix can include residues specific for four or more distinct tissues. The matrix is biocompatible and bioresorbable. Specifically, it is sufficiently free of pathogens and anti genic stimuli that can result in graft rejection. Preferably the matrix is derived from an allogenic or xenogenic body part. Preferably, it is derived from a mammalian donor, such as a cadaver, The body part may be rendered inert or "devitalized" by dehydration, such as by ethanol extraction and lyophilization, so that no residual cellular metabolism remains, but the function of endogenous growth factors and the like can be restored upon in situ reconstitution by endogenous body fluids. The treated body part which now is substantially depleted in antigenic and pathogenic components and now is biocompatible, maintains the residues specific for the plural distinct tissues constituting the body part sought to be replaced. These residues include those of plural distinct tissues with dimensions and structural relationships to each other which mimic those of the body part to be replaced.

The thus treated matrix having utility in the methods and devices of the invention lacks significant mechanical integrity as compared with native tissue and, on its own, is not sufficient to induce regeneration of a replacement body part or tissue when implanted. However, by impregnating or otherwise infusing the interstices of the matrix with osteogenic protein so that the protein is disposed on or adsorbed to, the surfaces of the matrix, the device of the instant invention is formed and is sufficient to induce formation of new tissue in vivo such that regeneration of a mechanically and functionally viable replacement body part occurs in situ.

In one preferred embodiment, the device comprises part or all of a skeletal joint excised from a mammalian donor allogenic or xenogenic to the donee. Treated as described herein the device comprising the allogenic or xenogenic skeletal joint (1) is biocompatible, namely, it is non-pathogenic and sufficiently non-antigenic to prevent graft rejection in vivo and (2) is sufficient to induce formation of a functionally viable autogenous replacement joint in vivo, including generating functional bone, articular cartilage, ligament and capsule tissue in correct relation to one another such that a structurally and mechanically functional replacement joint results.

In another embodiment, the invention provides a device which serves as a template for forming in vivo part or all of a skeletal synovial joint comprising plural distinct tissues and which, in response to morphogenic signals, induces new tissue formation, including new articular cartilage tissue from responding cells present in the synovial environment. The newly formed tissues assume the shape and function of the original tissue in the skeletal joint.

In another aspect, the invention provides methods for replacing a defective body part comprising the steps of: excising the defective body part and implanting the device of the instant invention. In one embodiment, the method also comprises the additional step of providing a supply of mesenchymal cells to the implanted device, as by threading or otherwise providing a muscle flap prefused with a blood supply into a hollow portion of the device. In another embodiment, the device is implanted at a locus in the body of the individual distinct from the defect site but which allows generation of the replacement body part. The autogenous body part thus formed then can he implanted at the defect site.

As will be appreciated from the description provided herein, in another aspect, the invention provides devices and methods for the functional and mechanical restoration of one or more individual tissues in a mammalian skeletal joint, including the non-mineralized and avascular tissue therein. Thus, in one embodiment, the invention provides methods and devices competent for restoring, without limitation, functional articular cartilage, ligament, synovial membrane and synovial capsule tissue. The methods and devices described herein can be used for example, to correct superficial articular cartilage defects in a joint, to replace torn or compromised ligaments and/or tendons, and to repair defects in synovial capsule or membrane tissue.

The devices for repairing individual skeletal joint tissue comprise osteogenic protein disposed on a matrix containing residues specific for, or derived from skeletal joint tissue of the type to be restored, including, without limitation, cartilage, ligament, tendon, synovial capsule, or synovial membrane tissue. The device can take the form of a solid, or it can have the physical properties of a paste or gel. Preferably, the matrix is derived from allogenic or xenogenic tissue, and is treated as described herein to form a biocompatible devitalized matrix.

In another embodiment the matrix can be formulated de novo from synthetic and/or naturally-derived components. The matrix includes both (a) residues specific for, or characteristic of, the given tissue and, (b) materials sufficient to create a temporary scaffold for infiltrating cells and defining a three dimensional structure which mimics the dimensions of the desired replacement tissue. Useful such materials are described herein below. Suitable tissue-specific residues can be obtained from devitalized allogenic or xenogenic tissue and combined with the structural materials as described herein to create the synthetic matrix. In another embodiment, the matrix comprises devitalized non-mineralized tissue. In some circumstances, as in the formation of articular cartilage on subchondral bone, a non-mineralized matrix material defining a three-dimensional structure which allows the attachment of infiltrating cells, can be sufficient, in combination with osteogenic protein, to induce new tissue formation.

While, as described above, in a preferred embodiment the invention contemplates a device suitable as a template for forming in vivo a replacement skeletal joint, as will be appreciated by the practioner in the art, the invention contemplates, and the disclosure enables, a device suitable as a template for forming in vivo functional replacement body parts other than skeletal joints and which comprise plural distinct tissues.

When used in accordance with the methods of the instant invention, the devices of the invention and/or the tissues which result from their application, essentially satisfy the following criteria of a preferred grafting material:

1. They result in formation of mechanically and functionally viable tissues normally present at the site. These tissues are of an appropriate size and have correct structural relationships so as to result in a functional body part. In particular, the multi-tissue replacement part, whether produced in situ at the site of intended use or remotely, becomes incorporated, integrating with adjacent tissues, essentially maintaining its shape, and avoiding abnormal resorption, regardless of the conditions present at the recipient site. Weiland et al. (1983) Clin. Orthop. 174:87 (1983).

2. The devices are capable of being precisely contoured and shaped to exactly match any defect, whichever complex skeletal or organ shape it is meant to replace.

3. The devices virtually have unlimited supply and are relatively easy to obtain.

4. The devices have minimal donor site morbidity.

Furthermore, the instant invention provides practitioners with materials and methods for skeletal joint repair including the repair of the bone and articular cartilage present therein, and which solve problems that occur using the methods and devices of the art. For example, the instant invention can induce formation of bona fide hyaline cartilage rather than fibrocartilage at a defect site. Using the materials and methods disclosed herein, functional hyaline cartilage forms on the articulating surface of bone at a defect site and does not degenerate over time to fibro-cartilage. By contrast, prior art methods of repairing cartilage defects generally ultimately result in development of fibrous cartilage at the defect site.

Unlike hyaline cartilage, fibrocartilage lacks the physiological ability to restore articulating joints to their full capacity. Thus, when the instant materials are used in accordance with the instant methods, the practitioner can substantially functionally restore a cartilage defect in an articulating joint, particularly a superficial articular cartilage defect and substantially avoid the undesirable formation of fibrocartilage typical of prior art methods, or degeneration into a "full-thickness defect". The invention also provides means for repairing individual tissue of a joint not readily reparable individually using prior art methods, and which, in some cases, previously warranted replacement of the entire joint with a prosthetic device. The invention further allows use of allogenic replacement materials for repairing the avascular tissue in a skeletal joint, and which result in the formation of mechanically and functionally viable replacement tissues at a joint locus.

BRIEF DESCRIPTION OF THE DRAWINGS

While the specification concludes with claims particularly pointing out and specifically claiming the subject matter which is regarded as constituting the present invention, it is believed that the invention will be better understood from the following detailed description of preferred embodiments taken in conjunction with the accompanying drawings in which:

FIG. 2A depicts a lyophilized allograft; FIG. 2B depicts osteogenic protein for application to the lyophilized allograft of FIG. 2A; FIG. 2C depicts a muscle flap of cutaneous maximus muscle to he threaded inside the shaft of the lyophilized allograft; and, FIG. 2D depicts a viable, functional hemi-joint resulting from the combination of elements in FIGS. 2A, 2B and 2C. FIG. 2D represents one embodiment of the device of the instant invention;

DETAILED DESCRIPTION

Figure 1:
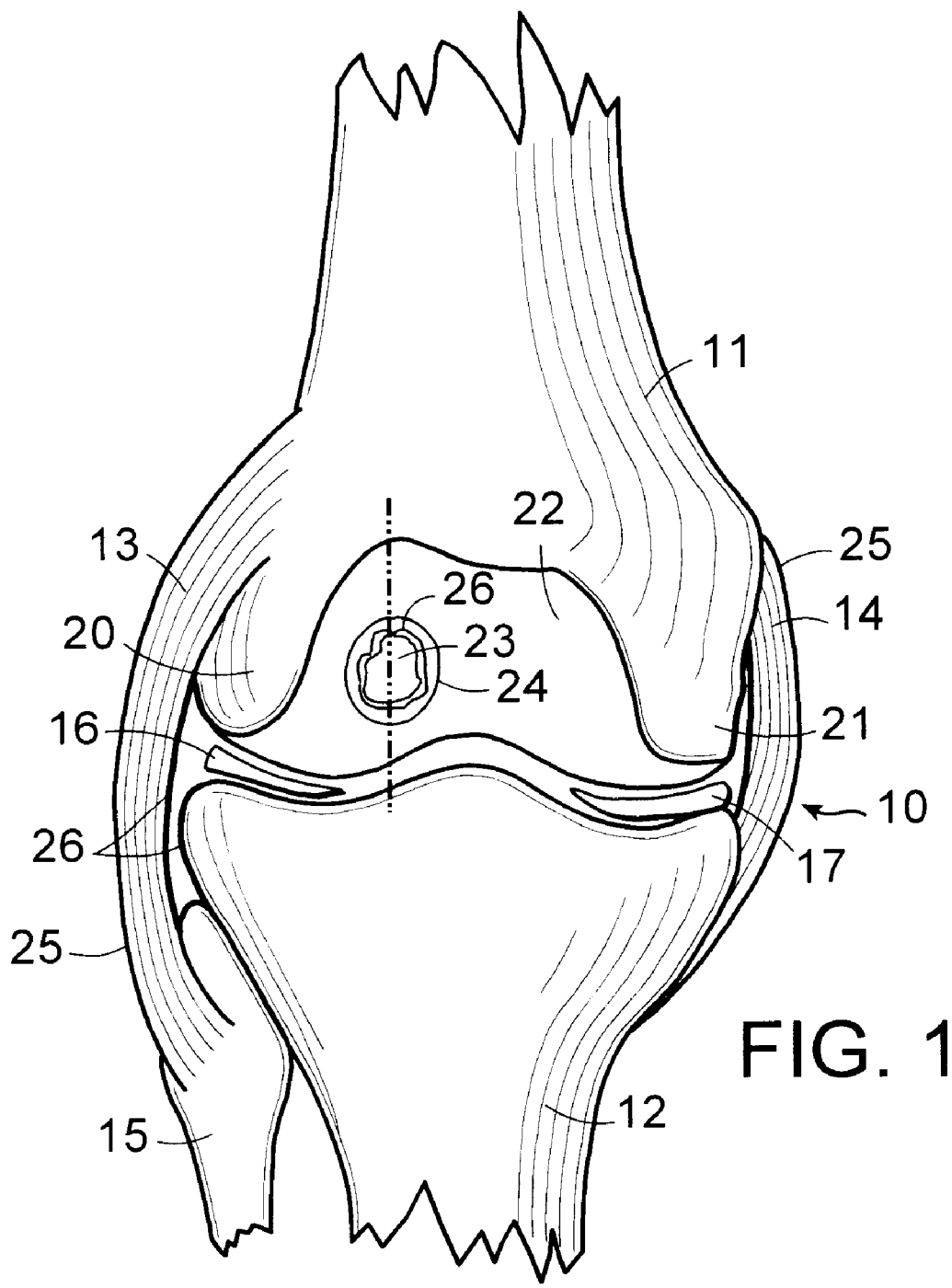
FIG. 1 is a fragmentary front elevational view of a mammalian knee joint with sufficient tissue removed to show the articular cartilage on the condyles of the femur, the ligaments, synovial membrane, joint capsule, and further showing a damaged area in the articular cartilage requiring repair.

In accordance with the present invention, novel materials and methods are provided for the repair and regeneration of plural distinct tissues, including manufacture of a live autogenous replacement part comprising plural distinct tissues. In one embodiment the replacement body part is a skeletal joint, particularly an articulating joint, and includes, without limitation, residues specific for, or derived from, bone, cartilage, ligament, tendon, synovial capsule and synovial membrane tissue.

More particularly, in one aspect, the invention provides a device comprising an osteogenic protein disposed on the surfaces of a matrix or substrate for terming a functional, mammalian replacement body part comprising plural distinct tissues. As used herein, the term "matrix" is understood to define a structure having interstices for the attachment, proliferation and differentiation of infiltrating cells. It comprises residues specific for the tissue to be replaced and/or derived from the same tissue type, and has a shape and dimension when implanted which substantially mimics that of the replacement tissue desired.

As used herein, the term "residue" is intended to mean a constituent of a given tissue, which has specificity for, or is characteristic of, the given tissue, and which is derivable from the non-viable constituents of the given tissue. A matrix comprising these residue(s), when combined with osteogenic protein, and implanted in a mammal in an environment which mimics the tissue's local environment under physiological conditions, and is sufficient for formation of specific, mechanically and functionally viable replacement tissue.

The term "plural distinct tissue" is intended to mean physiologically distinguishable tissues, such as biochemically or ultrastructurally distinguishable tissues which reside at an anatomically similar locus. In an articulating replacement joint device for example, the matrix can comprise residues specific for, or derived from, bone, cartilage, ligament, tendon and synovial membrane tissue. Thus, a significant aspect of the matrix of the invention is a single structure comprising residues of plural, distinct tissues, and which, when combined with an osteogenic protein as defined herein, is suitable for inducing repair or regeneration of a body part that is mechanically and functionally viable over time in vivo.

As used herein, the terms "bone" and "articular carlilage" are intended to mean the following: Bone refers to a calcified (mineralized) connective tissue primarily comprising a composite of deposited calcium and phosphate in the form of hydroxyapatite, collagen (predominantly Type I collagen) and bone cells, such as to osteoblasts, osteocytes and osteoclasts, as well as to the bone marrow tissue which forms in the interior of true endochondral bone. Cartilage refers to a type of connective tissue that contains chondrocytes embedded in an extracellular network comprising fibrils of collagen (predominantly Type II collagen along with other minor types, e.g. Types IX and XI), various proteoglycans (e.g., chondroitin sulfate, keratan sulfate, and dermatan sulfate proteoglycans), other proteins, and water. Articular cartilage refers to hyaline or articular cartilage, an avascular, non-mineralized tissue which covers the articulating surfaces of the portions of bones in joints and allows movement in joints without direct bone-to-bone contact, and thereby prevents wearing down and damage to opposing bone surfaces. Most normal healthy articular cartilage is referred to as "hyaline," i.e., having a characteristic frosted glass appearance. Under physiological conditions, articular cartilage tissue rests on the underlying, mineralized bone surface, the subchondral bone, which contains highly vascularized ossicles. These highly vascularized ossicles can provide diffusible nutrients to the overlying cartilages but not mesenchymal stem cells.

"Ligament" is intended to mean both the rope-like structures of white fibrous connective tissue which attach anterior extremities of intracting bones, as well as the tissue defining a synovial capsule. "Synovial membrane" is intended to define the connective tissue membrane lining the interior of the synovial cavity and which is involved in synovial fluid secretion. "Tendon" is intended to define the connective tissue structure which joins muscle to bone.

Replacement Body Parts

As disclosed herein, the instant invention provide methods and compositions for replacing and repairing a defective body part. The method comprises the steps of surgically excising the defective body part, implanting a device comprising a matrix of the type described above at the site of excision, and, as necessary, surgically repairing tissues adjacent the site of excision as described herein below. For example, for synovial joint replacement, it is desirable to repair the joint capsule, including the synovial membrane and ligaments, so as to surgically approximate the joint structure as it occurs under physiological conditions, thereby recreating the avascular environment which is the synovial cavity and which is bathed in synovial fluid. It also is preferable to suture or otherwise mechanically temporarily connect the implanted device to surrounding tissue.

In one embodiment the device is constructed to replace part or all of a mammalian skeletal joint structure and includes a matrix having residues for plural, distinct tissues, including two or more of bone, cartilage, ligament, tendon, synovial capsule and/or synovial membrane tissue.

In another embodiment the device is constructed to replace an individual tissue of a mammalian skeletal joint, including an individual avascular and/or non-mineralized tissue. As demonstrated herein, the device is competent to induce functional replacement tissue formation, including articular cartilage, from responding cells present in the local environment, including a synovial environment, and without requiring cellular infiltration of mesenchymal cells from a vascularized muscle flap. The matrix of this embodiment comprises residues specific for, or characteristic ot, and/or derived from, tissue of the same type as the individual tissue to be replaced. In another embodiment, the matrix comprises devitalized non-mineralized tissue. In a preferred embodiment, the replacement tissue can include articular cartilage, ligament, bone, tendon or synovial capsule tissue.

In a partial or complete joint replacement, it is preferred but not required to include in the practice of the method the additional step of threading a muscle flap into a hollow portion of the implanted device. For example, using the method described in Khouri, U.S. Pat. No. 5,067,963, the disclosure of which is incorporated herein by reference and herewith below, a muscle flap, which can itself be pretreated with osteogenic protein, can be surgically introduced into a cavity in the implanted matrix, such as the marrow cavity of devitalized bone, to provide a blood supply to expedite morphogenesis of vascularized tissue and to provide a ready supply of mesenchymal stem cells.

The matrix of instant invention has utility as an implantable device when osteogenic protein is disposed on the surfaces of the matrix, present in an amount sufficient to induce formation of each of the replacement tissues. This permits regeneration of the body part within the mammal, including plural tissues of appropriate size, interrelationship, and function. Osteogenic proteins contemplated to be useful in the instant invention are described below and have been earlier-described in, for example, U.S. Pat. Nos. 4,968,550, 5,258,494 and 5,266,683, the disclosures of which are incorporated by reference herein. The osteogenic protein can be, for example, any of the known bone morphogenetic proteins and/or equivalents thereof described herein and/or in the art and includes naturally sourced material, recombinant material, and any material otherwise produced which is capable of inducing tissue morphogenesis.

The methods and materials of the instant invention are especially useful for the repair and/or partial or complete replacement of mammalian body joints, including, without limitation, articulating joints, particularly joints enclosed by a ligamentous capsule and bathed in synovial fluid.

In some synovial joints, the movement is uniaxial, i.e., all movements take place around one axis: Among these are the ginglymus or hinge joint in which the axis of movement is transverse to the axes of the bones, and the trochoid or pivot joint in which the axis is longitudinal. In the case of biaxial synovial joints, movements are around two axes at a right angle or any other angle to each other: These include the condyloid, the ellipsoid, and the saddle joints. There is a third type of synovial joint, the spheroidal or ball-and-socket joint, in which the movements are polyaxial, i.e., movements are permitted in an infinite number of axes. Finally, there are the plane or gliding-type synovial joints.

In hinge joints, the articular surfaces are molded to each other in such a manner as to permit motion in only one plane around the transverse axis. Flexion at the elbow joint is an example; other examples include the interphalangeal joints of both the fingers and toes. In pivot joints, movement in a pivot joint also occurs around a single axis, however, it is the longitudinal axis. There are several pivot joints in the human body, such as the proximal radioulnar articulation. In condylar joints include, movement occurs principally in one plane. The tibiofemoral articulation of the knee joint is an example. In ellipsoid joint include, movement is around two principal axes which are at right angles to each other. Examples of these joints include the radiocarpal and metacarpophalangeal joints. In a saddle joint, the articular end of the proximal bone is concave in one axis and convex in a perpendicular axis. These surfaces fit reciprocally into convex and concave surfaces of the distal bone. The best example of a saddle joint is the carpometacarpal joint of the thumb. A ball-and-socket joint is one in which the distal bone is capable of motion around an indefinite number of axes with one common center. Examples of this form of articulation are found in the hip and shoulder joints. A plane or gliding-type joint allows a slight slipping or sliding of one bone over the other. Unlike the above-described joints, the amount of motion between the surfaces is limited by the ligaments or osseous processes that surround the articulation. This is the form present in the joints between the articular processes of certain vertebrae, the carpal joints, and the intermetatarsal joints.

Although it is contemplated that the present invention is usable to repair defects including bone and articular cartilage elsewhere in a mammalian body, aspects of the invention are here illustrated in connection with the articulating surfaces on the femur in a knee joint 10 illustrated in FIG. 1.

FIG. 1 illustrates a knee joint 10 between die bottom of a femur 11 and the top of a tibia 12. For clarity of illustration, only portions 13 and 14 of the medial and lateral collateral ligaments which movably tie the femur 11 to the underlying tibia 12 and fibula 15, are shown in FIG. 1. Similarly, the joint capsule is represented by the exterior dark lining 25, and the synovial membrane, which lines the synovial cavity and secretes the lubricating synovial fluid, is represented by the interior dark lining 26. Normally interposed between the opposing surfaces of the femur 11 and tibia 12 are lateral and medial meniscus cartilages 16 and 17 and anterior and posterior cruciate ligaments (not shown). The convexly curved condyles 20 and 21 at the lower end of the femur 11 are normally supported by the meniscus cartilages 16 and 17, respectively, on the upper end of the tibia 12. Normally, the lower end of the femur 11, including the condyles 20 and 21, are covered by a layer 22 of hyaline cartilage material, referred to as the articular cartilage 22. The articular cartilage 22 forms a generally resilient padding which is fixed on the surface of the lower end of the femur 11 to protect the latter from wear and mechanical shock. Moreover, the articular cartilage 22, when lubricated by the synovial fluid in the knee joint 10, provides a surface which is readily slidable on the underlying surfaces of the meniscus cartilages 16 and 17 (or on the upper surface of the tibia 12 should one or both of the meniscus cartilage 16 and 17 be partly or totally absent) during articulation of the knee joint 10.

A portion of the articular cartilage may become damaged by injury or disease, or become excessively worn. FIG. 1 illustrates an example of a damaged area 23.

Matrix Considerations

As will be appreciated by the skilled artisan, provided the matrix has a three dimensional structure sufficient to act as a scaffold for infiltrating cells, and includes the residues specific for, or characteristic of, and/or which are derived from, the same tissue type as the tissue to be repaired, the precise nature of the substrate per se used for the matrices disclosed herein is not determinative of a matrix's ultimate ability to repair and regenerate replacement tissue. In the instant invention, the substrate serves as a scaffold upon which certain cellular events, mediated by an osteogenic protein, necessarily will occur. The specific responses to the osteogenic protein ultimately are dictated by the endogenous microenvironment at the implant site and the developmental potential of the responding cells. As also will be appreciated by the skilled artisan, the precise choice of substrate utilized for the matrices disclosed herein will depend, in part, upon the type of defect to be repaired, anatomical considerations such as the extent of vascularization at the defect site, and the like.

The matrix of the invention may be obtained as follows. A replacement tissue or body part to be used as a replacement body part and which comprises at least two distinct tissues in association to form the body part, is provided, as from a cadaver, or from a bone bank and treated, as by ethanol treatment and dehydrated by lyophilization, so that the remaining material is non-pathogenic and sufficient non-antigenic to prevent graft rejection. As described above, the thus treated material having utility in the devices of the invention further comprises the residues of the extracted tissue or tissues from which it is derived. A replacement body part matrix thus treated further is dimensioned such that the residues have a structural relationship to each other which mimic that of the body part to be replaced.

Natural-sourced Matrices

Suitable allogenic or xenogenic matrices can be created as described herein below, using methods well known in the art. Preferably, the replacement body part or tissue is obtained fresh, from a cadaver or from a tissue bank which freezes its tissues upon harvest. In all cases and as will be appreciated by the practitioner in the field, it is preferable to freeze any tissue upon harvest, unless the tissue is to be put to immediate use. Prior to use, the tissue is treated with a suitable agent to extract the cellular non-structural components of the tissue so as to devitalize the tissue. The agent also should be capable of extracting any growth inhibiting components associated with the tissue, as well as to extract or otherwise destroy any pathogens. The resulting material is an acellular matrix defining interstices that can be infiltrated by cells, and is substantially depleted in non-structurally-associated components.

In a currently preferred procedure, the tissue is devitalized following a methodology such as that used in the art for fixing tissue. The tissue is exposed to a non-polar solvent, such as 100% (200 proof) ethanol, for a time sufficient to substantially replace the water content of the tissue with ethanol and to destroy the cellular structure of the tissue. Typically, the tissue is exposed to 200 proof ethanol for several days, at a temperature in the range of about 4°–40° C., taking care to replace the solution with fresh ethanol every 6–12 hours, until such time as the liquid content of the tissue comprises 70–90% ethanol. Typically, treatment for 3–4 days is appropriate. The volume of liquid added should be more than enough to submerge the tissue. The treated tissue then is lyophlized. The resulting, dry matrix is substantially depleted in non-structural components but retains both intracellular and extracellular matrix components derived from the tissue.

Numerous other methods are described in the art for extracting tissues, including mineralized tissue such as bone, and for rendering these tissues biocompatible for allogenic or xenogenic implants. See, for example, Sampath et at. (1983) PNAS 80:6591–6595, U.S. Pat. No. 5,011,691, and U.S. Pat. Nos. 4,975,526 and 5,171,574. These publications describe extraction with 4M guanidine-HCl, 50 mM Tris-HCl, pH 7.0 for 16 hours at 4° C., and various deglycosylating and collagen fibril modifying agents, including hydrogen fluoride, trifluorocetic acid, dichloromethane, acetonitrile, isopropanol, heated, acidic aqueous solutions, and various combinations of these reagents. The disclosures of the patents is incorporated herein by reference. As described therein and below, where the matrix is treated with a fibril-modifying agent, the treated matrix can be washed to remove any extracted components, following a form of the procedure set forth below:

1. Suspend matrix preparation in TBS (Tris-buffered saline) 1 g/200 ml and stir at 4° C. for 2 hrs; or in 6 M urea, 50 mM Tris-HCl, 500 mM NaCl, pH 7.0 (UTBS) or water and stir at room temperature (RT) for 30 minutes (sufficient time to neutralize the pH);
2. Centrifuge and repeat wash step; and
3. Centrifuge; discard supernatant; water wash residue; and then lyophilize.

Treated allogenic or xenogenic matrices are envisioned to have particular utility for creating devices for forming replacement body parts comprising plural distinct tissues, as well as for creating devices for replacing individual joint tissues, such as ligament and articular cartilage tissue. For example, a replacement ligament device can be formulated from an allogenic ligament matrix and osteogenic protein, and implanted at a skeletal joint locus following standard surgical procedures for autogenous ligament replacement. Similarly, an allogenic articular cartilage device can be formed from devitalized cartilage tissue, or other inert, non-mineralized matrix material and osteogenic protein, and the device laid on the subchondral bone surface as a sheet. Alternatively, a formulated device can be pulverized or otherwise mechanically abraded to produce particles which can be formulated into a paste or gel as described herein for application to the bone surface.

Synthetic Matrices

As an alternative to a natural-sourced matrix, or as a supplement to be used in combination with a natural-sourced matrix, a suitable matrix also can be formulated de novo, using (1) residues derived from and/or characteristic of, or specific for, the same tissue type as the tissue to be repaired, and (2) one or more materialswhich serve to create a three-dimensional scaffolding structure that can be formed or molded to take on the dimensions of the replacement tissue desired. In some circumstances, as in the formation of articular cartilage on a subchondral bone surface, osteogenic protein in combination with a matrix defining a three-dimensional scaffolding structure sufficient to allow the attachment of infiltrating cells and composed of a non-mineralized material can be sufficient. Any one or combination of materials can be used to advantage, including, without limitation, collagen; homopolymers or copolymers of glycolic acid, lactic acid, and butyric acid, including derivatives thereof; and ceramics, such as hydroxyapatite, tricalcium phosphate and other calcium phosphates and combinations thereof.

The tissue-specific component of a synthetic matrix readily can be obtained by devitalizing an allogenic or xenogenic tissue as described above and then pulverizing or otherwise mechanically breaking down the insoluble matrix remaining. This particulate material then can be combined with one or more structural materials, including those described herein. Alternatively, tissue-specific components can be further purified from the treated matrix using standard extraction procedures well characterized in the art and, using standard analysis procedures, the extracted material at each purification step can be tested for its tissue-specificity capability. See, for example, Sampath et al. (1987) PNAS 78:7599–7603 and U.S. Pat. No. 4,968,590 for exemplary tissue extraction protocols.

A synthetic matrix may be desired where, for example, replacement articular cartilage is desired in an existing joint to, for example, correct a tear or limited superficial defect in the tissue, or to increase the height of the articular cartilage surface now worn due to age, disease or trauma. Such "resurfacing" of the articular cartilage layer can be achieved using the methods and compositions of the invention by, in one embodiment, treating a sheet of allogenic or xenogenic articular cartilage tissue as described herein, coating the resulting matrix with osteogenic protein, rolling up the formulated device so that it can be introduced to the joint using standard orthoscopic surgical techniques and, once provided to the site, unrolling the device as a layer onto the articular bone surface. In another embodiment, the device is formulated as a paste or injectable gel-like substance that can be injected onto the articular bone surface in the joint also using standard orthoscopic surgical techniques. In this embodiment, the formulation may comprise a pulverized or otherwise mechanically degraded device comprising both matrix and osteogenic protein and, in addition, one or more components which serve to bind the particles into a paste-like or gel-like substance. Binding materials well characterized in the art include, for example, carboxymethylcellulose, glycerol, polyethylene-glycol and the like. Alternatively, the device can comprise osteogenic protein dispersed in a synthetic matrix which provides the desired physical properties. As an example, a synthetic matrix having tissue specificity for cartilage and bone is described in WO91/18558, published Dec. 21, 1991 and herein below. Briefly, the matrix comprises a porous crosslinked structural polymer of biocompatible, biodegradable collagen and appropriate, tissue-specific glycosaminoglycans as tissue-specific cell attachment factors. Collagen derived from a number of sources can be used, including insoluble collagen, acid-soluble collagen, collagen soluble in neutral or basic aqueous solutions, as well as those collagens which are commercially available.

Glycosaminoglycans (GAGs) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexoamines glycosidically bound and alternating in a more-or-less regular manner with either hexouronic acid or hexose moieties (see, e.g., Dodgson et al. in Carbohydrate Metabolism and its Disorders (Dickens et al., eds.) Vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs also can be used for forming the matrix described herein, and those skilled in the art will either know or be able to ascertain other suitable GAGs using no more than routine experimentation. For a more detailed description of mucopolysaccharides, see Aspinall, *Polysaccharides,* Pergamon Press, Oxford (1970).

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although crosslinking by a dehydrothermal process is preferred.

Formulation Considerations

The devices of the invention can be formulated using any of the methods described in the art for formulating ostegenic devices. See, for example, U.S. Pat. No. 5,266,683, the disclosure of which is incorporated herein by reference. Briefly, osteogenic protein typically is dissolved in a suitable solvent and combined with the matrix. The components are allowed to associate. Typically, the combined material then is lyophilized, with the result that the osteogenic protein is disposed on, or adsorbed to the surfaces of the matrix. Useful solubilizing solvents include, without limitation, an ethanoltrifluoroacetic acid solution, e.g., 47.5% EtOH/ 0.01% TFA; and acetonitrile/TFA solution, ethanol or ethanol in water, and physiologically buffered saline solutions. Formulations in an acidic buffer can faciliate adsorption of OP1 onto the matrix surface. For the replacement body part devices of the invention, the currently preferred formulation protocol is incubation of matrix and osteogenic protein in an ethanol/TFA solution (e.g., 30–40% EtOH/0.01–0.1%TFA) for 24 hours, followed by lyophilization. This procedure is sufficient to adsorb or precipitate 70–90% of the protein onto the matrix surface.

The quantity of osteogenic protein used will depend on the size of replacement device to be used and on the specific activity of the osteogenic protein. Typically, 0.5 mg–100 mg/10 g of matrix, dry weight, can be used to advantage.

In addition to osteogenic proteins, various growth factors, hormones, enzymes, therapeutic compositions, antibiotics, or other bioactive agents also can be adsorbed onto, or impregnated within, a substrate and released over time when implanted and the matrix slowly is absorbed. Thus, various known growth factors such as EGF, PDGF, IGF, FGF, TGF-a, and TGF-b can be released in vivo. The matrix can also be used to release chemotherapeutic agents, insulin, enzymes, enzyme inhibitors or chemotactic-chemoattractant factors.

Protein Considerations

As defined herein, the osteogenic proteins useful in the composition and methods of the invention include the family of dimeric proteins having endochondral bone activity when implanted in a mammal in association with a matrix and which comprise a subclass of the "super family" of "TGFP-like" proteins. The natural-sourced osteogenic protein in its mature, native form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptides having molecular weights of about 14 kDa to 16 kDa capable of inducing endochondral bone formation in a mammal. Useful sequences include those comprising the C-terminal 102 amino acid sequences of DPP (from Drosophila), Vgl (from Xenopus), Vgr-1 (from mouse), the OP1 and OP2 proteins, proteins (see U.S. Pat. No. 5,011,691 and Oppermann et al., as well as the proteins referred to as BMP2, BMP3, BMP4 (see WO88/00205, U.S. Pat. No. 5,013,649 and WO91/18098), BMP5 and BMP6 (see WO90/11366, PCT/US90/01630 and BMP8 and 9.

The members of this family of proteins share a conserved six or seven cysteine skeleton in the C-terminal region. See, for example, 335–431 of Seq. ID No. 1 and whose sequence defines the six cysteine skeleton residues referred to herein as "OPS", or residues 330–431 of Seq. ID No. 1, comprising 102 amino acids and whose sequence defines the seven cysteine skeleton.

This family of proteins includes longer forms of a given protein, as well as phylogenetic, e.g., species and allelic variants and biosynthetic mutants, including addition and deletion mutants and variants, such as those which may alter the conserved C-terminal cysteine skeleton, provided that the alteration still allows the protein to form a dimeric species having a conformation capable of inducing bone formation in a mammal when implanted in the mammal in association with a matrix. In addition, the osteogenic proteins useful in devices of this invention may include forms having varying glycosylation patterns and varying N-termini, may be naturally occurring or biosynthetically derived, and may be produced by expression of recombinant DNA in procaryotic or eucaryotic host cells. The proteins are active as a single species (e.g., as homodimers), or combined as a mixed species, including heterodimers.

In one embodiment, the osteogenic protein contemplated herein comprises OP1 or an OP1-related sequence. Useful OP1 sequences are recited in U.S. Pat. Nos. 5,011,691; 5,018,753 and 5,266,683; in Ozkaynak et al. (1990) *EMBO J* 9:2085–2093; and Sampath et al. (1993) *PNAS* 90: 6004–6008. OP-1 related sequences include xenogenic homologs, e.g.; 60A, from Drosophila, Wharton et al. (1991) *PNAS* 88:9214–9218; and proteins sharing greater than 60% identity with OP1 in the C-terminal seven cysteine domain, preferably at least 65% identity. Examples of OP-1 related sequences include BMP5, BMP6 (and its species homolog Vgr-1, Lyons et al. (1989) *PNAS* 86:4554–4558), Celeste, et al. (1990) *PNAS* 87:9843–9847 and PCT international application WO93/00432; OP-2 (Ozkaynak et al. (1992) *J.Biol. Chem.* 267:13198–13205) As will be appreciated by those having ordinary skill in the art, chimeric constructs readily can be created using standard molecular biology and mutagenesis techniques combining various portions of different morphogenic protein sequences to create a novel sequence, and these forms of the protein also are contemplated herein.

In another preferred aspect, the invention contemplates osteogenic proteins comprising species of polypeptide chains having the generic amino acid sequence herein referred to as "OPX" which accommodates the homologies between the various identified species of the osteogenic OP1 and OP2 proteins, and which is described by the amino acid sequence presented below and in Sequence ID No. 3.

```
Cys Xaa Xaa His Glu Leu Tyr Val Ser Phe
 1       5               10
Xaa Asp Leu Gly Trp Xaa Asp Trp Xaa Ile
             15              20
Ala Pro Xaa Gly Tyr Xaa Ala Tyr Tyr Cys
             25              30
Glu Gly Glu Cys Xaa Phe Pro Leu Xaa Ser
             35              40
Xaa Met Asn Ala Thr Asn His Ala Ile Xaa
             45              50
Gln Xaa Leu Val His Xaa Xaa Xaa Pro Xaa
             55              60
Xaa Val Pro Lys Xaa Cys Cys Ala Pro Thr
             65              70
Xaa Leu Xaa Ala Xaa Ser Val Leu Tyr Xaa
             75              80
Asp Xaa Ser Xaa Asn Val Ile Leu Xaa Lys
             85              90
Xaa Arg Asn Met Val Val Xaa Ala Cys Gly
             95             100
    Cys His,
``` and wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Sere or Asn); Xaa at res. 89=(Lys or Arg); Xaa at res. 91=(Tyr or His); and Xaa at res. 97=(Arg or Lys).

In still another preferred aspect, one or both of the polypeptide chain subunits of the osteogenerically active dimer is encoded by nucleic acids which hybridize to DNA or RNA sequences encoding the active region of OP1 under stringent hybridization conditions. As used herein, stringent hybridization conditions are defined as hybridization in 40% formamide, 5× SSPE, 5× Denhardt's Solution, and 0.1% SDS at 37° C. overnight, and washing in 0.1× SSPE, 0.1% SDS at 50° C.

Given the foregoing amino acid and DNA sequence information, the level of skill in the art, and the disclosures of numerous publications on osteogenic proteins, including U.S. Pat. No. 5,011,691 and published PCT specification U.S. Ser. No. 89/01469, published Oct. 19, 1989, various DNAs can be constructed which encode at least the active domain of an osteogenic protein useful in the devices of this invention, and various analogs thereof (including species and allelic variants and those containing genetically engineered mutations), as well as fusion proteins, truncated forms of the mature proteins, deletion and addition mutants, and similar constructs which can be used in the devices and methods of the invention. Moreover, DNA hybridization probes can be constructed from fragments of any of these proteins, or designed de novo from the generic sequence. These probes then can be used to screen different genomic and cDNA libraries to identify additional osteogenic proteins useful in the prosthetic devices of this invention.

The DNAs can be produced by those skilled in the art using well known DNA manipulation techniques involving genomic and cDNA isolation, construction of synthetic DNA from synthesized oligonucleotides, and cassette mutagenesis techniques. 15–100mer oligonucleotides may be synthesized on a DNA synthesizer, and purified by polyacrylamide gel electrophoresis (PAGE) in Tris-Borate-EDTA buffer. The DNA then may be electroeluted from the gel. Overlapping oligomers may be phosphorylated by T4 polynucleotide kinase and ligated into larger blocks which may also be purified by PAGE.

The DNA from appropriately identified clones then can be isolated, subcloned (preferably into an expression vector), and sequenced. Plasmids containing sequences of interest then can be transfected into an appropriate host cell for protein expression and further characterization. The host may be a procaryotic or eucaryotic cell since the former's inability to glycosylate protein will not destroy the protein's morphogenic activity. Useful host cells include E. coli, Saccharomyces, the insect/baculovirus cell system, myeloma cells, CHO cells and various other mammalian cells. The vectors additionally may encode various sequences to promote correct expression of the recombinant protein, including transcription promoter and termination sequences, enhancer sequences, preferred ribosome binding site sequences, preferred mRNA leader sequences, preferred signal sequences for protein secretion, and the like.

The DNA sequence encoding the gene of interest also may be manipulated to remove potentially inhibiting sequences or to minimize unwanted secondary structure formation. The recombinant osteogenic protein also may be expressed as a fusion protein. After being translated, the protein may be purified from the cells themselves or recovered from the culture medium. All biologically active protein forms comprise dimeric species joined by disulfide bonds or otherwise associated, produced by folding and oxidizing one or more of the various recombinant polypeptide chains within an appropriate eucaryotic cell or in vitro after expression of individual subunits. A detailed description of osteogenic proteins expressed from recombinant DNA in E. coli and in numerous different mammalian cells is disclosed in U.S. Pat. No. 5,266,963, the disclosure of which is hereby incorporated by reference.

Alternatively, osteogenic polypeptide chains can be synthesized chemically using conventional peptide synthesis techniques well known to those having ordinary skill in the art. For example, the proteins may be synthesized intact or in parts on a solid phase peptide synthesizer, using standard operating procedures. Completed chains then are deprotected and purified by HPLC (high pressure liquid chromatography). If the protein is synthesized in parts, the parts may be peptide bonded using standard methodologies to form the intact protein. In general, the manner in which the osteogenic proteins are made can be conventional and does not form a part of this invention.

Exemplification

The means for making and using the matrices and devices of the invention, as well as other material aspects concerning the nature and utility of these compositions, including how to make and how to use the subject matter claimed, will be further understood from the following, which constitutes the best mode currently contemplated for practicing the invention. It will be appreciated that the invention is not limited to such exemplary work or to the specific details set forth in these examples.

In the exemplification, a hemi-joint reconstruction of an articulating synovial joint is resected into an existing joint locus. As will be appreciated by those having ordinary skill in the art, the methods and compositions of the invention equally can be applied to the formation of replacement body parts other than skeletal joints, as well as to skeletal joints other than articulating or synovial joints. Moreover, if desired, a replacement autogenous joint can be constructed in the recipient first by placing the device of the invention at another convenient locus distal to the defect site, for a time sufficient to induce formation of the replacement body part, and the autogenous body part thus formed then sutured into the joint locus for use.

EXAMPLE 1

Reconstruction of a Mammalian Hemi-Joint

New Zealand white rabbits were used as the experimental model. Standard orthopedic surgical equipment and procedures were used.

Figure 2D:
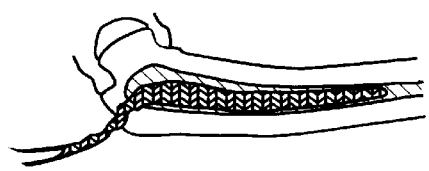
FIGS. 2A through 2D are schematic representations of the elements used to generate a viable, functional glenohumoral hemi-joint in one embodiment of the invention.
Figure 2C:
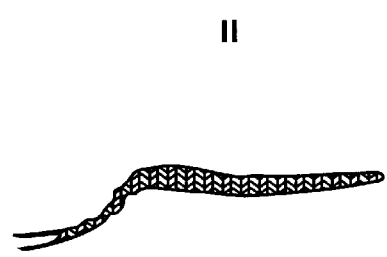
Figure 2B:
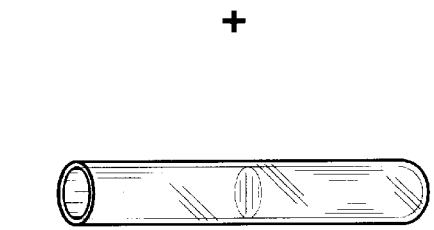
Figure 2A:
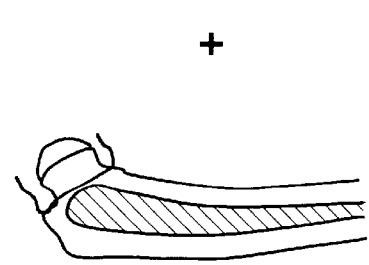

As depicted in FIG. 2A, joint defects were created in a recipient by surgically resecting the entire gleno-humeral hemiarticular complex with the proximal two-thirds of the humerus. Allografts for implantation were prepared from hemi-joints excised from a donor animal with the articular surface of the glenohumoral joint. All allografts were extracted in ethanol and lyophilized using standard procedures, and as described herein above, to destroy the pathogenicity and antigenicity of the material. Specifically, intact joint complexes were excised, demarraowed and ethanol treated by exposure to 200ml–500ml of 200 proof ethanol for 72 hours at 40 C. Fresh ethanol was provided every 6–8 hours. Following ethanol treatment, the matrix was lyophilized and rehydrated in ethanol/TFA, with or without osteogenic protein. The treated hemi-joints comprised devitalized bone, articular cartilage, ligament, tendon, synovialcapsule and synovial membrane tissue.

As illustrated in FIG. 2B, all lyophilized, osteogenic protein-treated allografts were coated with OP-1 as described in U.S. Pat. No. 5,011,691. Specifically, mature, dimeric recombinant OP-1 (rhOP1) was solubilized in an acetonitrile trifluoro-acetic acid solution, combined with the lyophilized allograft, and implanted. 15–20 mg protein/8–10 g matrix, dry weight, was used. The distal bone portions of all allografts were secured in place with a four hole titanium miniplate. A meticulous surgical reconstruction of the joint capsule was performed by suturing the lyophilized capsule ends to the endogenous capsule using standard surgical procedures well established in the art. This recreated an intact capsule and synovial lining, thereby restoring the synovial milieu of the grafted articular surface. Motion was permitted almost immediately after surgery, again to restore normal joint conditions.

In some animals, local muscle flaps (cutaneous maximus muscle; FIG. 2C) were incorporated into the region of the defect by threading muscle into the marrow cavity of the allograft as depicted in FIG. 2D, using the method of Khouri as described in U.S. Pat. No. 5,067,963 the disclosure of which is incorporated herein by reference. Briefly, vascularized and convenient muscle flaps were dissected using standard procedures well known to the practitioner in reconstructive surgery, so as to maintain a perfusing blood supply, and threaded inside the bone marrow cavities of the allografts.

Preliminary evaluations of the reconstructed hemi-joints were obtained by serial weekly radiographs using X-ray, and/or magnetic resonance imaging (MRI). Histological and mechanical confirmatory evaluations were conducted upon sacrifice at 5 weeks and 6 months after surgery.

Mechanical evaluations involved standard range of motion (ROM) measurements obtained serially until sacrifice. Histological evaluations involved staining sagital sections through the harvested allografts using standard techniques.

Briefly, identification of bona fide articular cartilage can be accomplished using ultrastructural and/or biochemical parameters. For example, articular cartilage forms a continuous layer of cartilage tissue possessing identifiable zones. The superficial zone is characterized by chondrocytes having a flattened morphology and an extracellular network which does not stain, or stains poorly, with toluidine blue, indicating the relative absence of sulphated proteoglycans. Chondrocytes in the mid and deep zones have a spherical appearance and the matrix contains abundant sulphated proteoglycans, as evidenced by staining with toluidine blue. Collagen fibers are present diffusely throughout the matrix. The chondrocytes possess abundant rough endoplasmic reticulum and are surrounded by extracellular network. The pericellular network contains numerous thin non-banded collagen fibers. The collagen in the interterritorial network is less compacted and embedded in electron translucent amorphous material, similar to articular cartilage. Collagen fibers in the interterritorial region of the network exhibit the periodic banding characteristic of collagen fibers in the interterritorial zone of cartilage tissue.

Biochemically, the presence of Type II and Type IX collagen in the cartilage tissue is indicative of the differentiated phenotype of chondrocytes. The presence of Type II and/or Type IX collagen can be determined by standard gel electrophoresis, Western blot analysis and/or immunohistochemical staining using, for example, commercially available antibody. Other biochemical markers include hematoxylin, eosin, Goldner's Trichrome and Safranin-O.

Articular cartilage regeneration was evaluated histologically in the examples described herein using glycosaminoglycan-specific stains and techniques well-known in the art. For the initial histologic evaluation, the defect sites were bisected lengthwise through the center of the defect. The resulting halves and surrounding tissue were embedded in paraffin and sectioned across the center of the defect. One half of each defect was utilized for histological staining with toluidine blue and/or hematoxlin and eosin, Goldner's Trichrome and Safranin-O. The other half was used in preparing sections for immunostaining. Histological evaluations involved assessment of: glycosaminoglycan content in the repair cartilage; cartilage and chondrocyte morphology; and, structural integrity and morphology at the defect interface. The morphology of the repair cartilage was exhibited for the type of cartilage formed: articular vs. fibrotic by evaluating glycosaminoglycan content, degree of cartilage deposition, and the like.

Histological evaluations using standard methodologies well characterized in the art also allows assessment of new bone and bone marrow formation. See, for example, U.S. Pat. No. 5,266,683, the disclosure of which is incorporated hereinabove by reference. Similarly, ligament and synovial capsule integrity can be montiored by MRI, as well as by histology upon sacrifice.

EXAMPLE 2

Five Weeks Duration (Short Term)

Figure 3D:
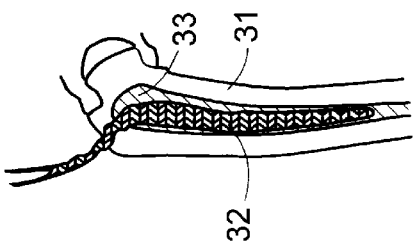
FIGS. 3A through 3D are schematic representations of the four allografts tested in the hemi-joint of Example 2 (5 week)
Figure 3C:
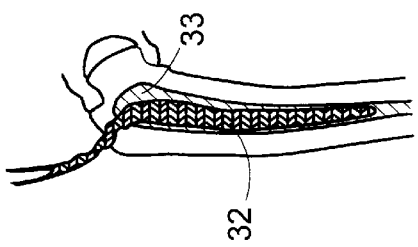
Figure 3B:
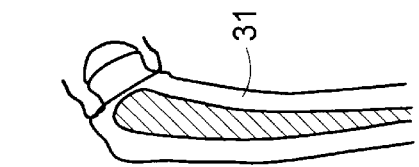
Figure 3A:
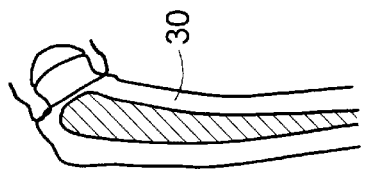

For the 5 week study, four groups with 10 rabbits per group were implanted with lyophilized allografts. See FIGS. 3A, 3B, 3C, and 3D. In Group 1, control lyophilized allograft 30 free of osteogenic protein, was implanted (FIG. 3A). In Group 2, experimental lyophilized allograft 31 was impregnated with OP-1 prior to implantation (FIG. 3B). In Group 3, control lyophilized allograft 30 free of osteogenic protein, was implanted, with muscle flap 32 threaded into marrow cavity 33 (FIG. 3C). In Group 4, experimental lyophilized allograft 31 was impregnated with OP-1 prior to implantation, and muscle flap 32 was threaded within the marrow cavity 33 (FIG. 3D). As stated above, graft healing was followed non-invasively with serial X-rays and standard MRI (magnetic resonance imaging). By X-ray assessment, allografts treated with osteogenic protein had a noticeably thickened cortex by 1 week post-operative, as compared with control allografts (Groups 1, 3) which evidenced only a thin egg-shell-like cortex. By four weeks the majority control allografts had fractured and were unstable. In contrast, OP-1 treated allografts (Groups 2, 4) remained stable.

MRI also was used as a non-invasive means for following reformation of articular cartilage in the allografts. A dark signal produced by MRI represents absent or nonviable cartilage, while a bright signal indicates live, viable cartilage. Control allografts produced only a dark signal, when tested at 1, 3 and 5 weeks post-operative. These MRI findings were confirmed by histological analysis performed at 5 weeks post-operative. Sagital sectioning through control allografts showed a degenerated articular surface with no live cells.

By contrast, the MRI findings of the articular caps from OP-1-treated allografts showed a bright signal by week 3 post-operative, indicating regeneration of viable articular cartilage. Histological analysis of the OP-1-treated allografts at week 5 revealed a layer of newly generated articular cartilage on top of the allograft matrix. The allografts of Group 4 showed somewhat thicker cartilage layers than those of Group 2, suggesting that the addition of the muscle flap may further enhance the rate of joint regeneration.

Additionally, joints regenerated with the OP-1-treated allografts regained near normal range of motion by the time they were harvested at 5 weeks post-reconstruction. The near normal range of motion also is indicative of the presence of lubricating synovial fluid. By contrast, the harvested control allografts were stiff and contracted at harvest. Thus, hemi-joint replacement devices of the invention succeeded in forming mechanically and functionally viable replacement joints, with an intact capsule, and synovium, and functioning ligament, bone and articular cartilage tissue. In the absence of osteogenic protein, the allografts, while not rejected by the donor, are insufficient on their own to generate a functional, weight bearing joint.

EXAMPLE 3

Six Months Duration—(Long Term)

For the 6 month study, the variable of shaving off the old cartilaginous cap in the lyophilized allografts was introduced. Briefly, this was accomplished by mechanically shaving the articular cartilage cap of the joint surface.

Figure 4A:
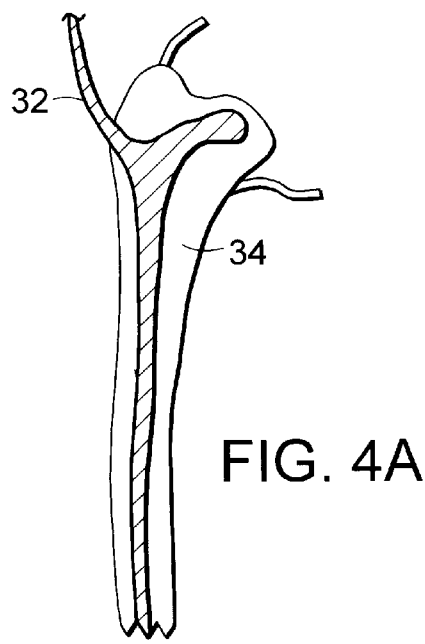
FIGS. 4A through 4D are schematic representations of the four allografts tested in the hemi-joint of Example 3 (6 month).
Figure 4B:
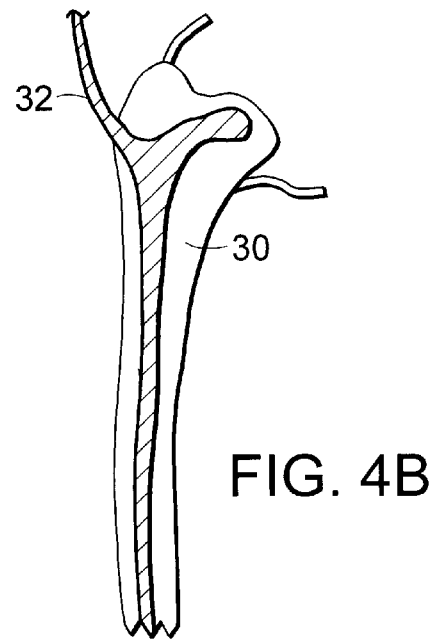
Figure 4C:
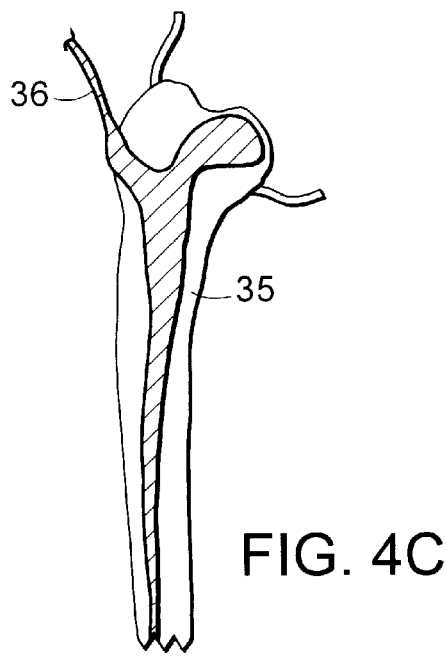
Figure 4D:
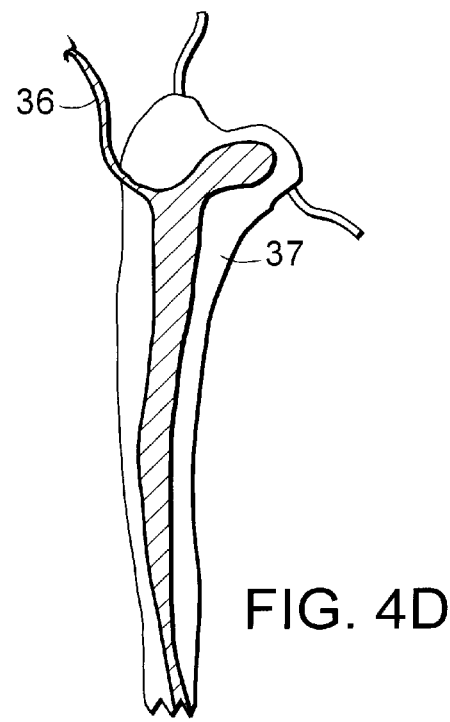

The following groups were used with 4 rabbits per group: in Group 5, lyophilized allograft 34 with shaved articular surface, and muscle flap 32 were implanted (see FIG. 4A); in Group 6, control lyophilized allograft 30 with non-shaved articular surface, and muscle flap 32 were implanted (see FIG. 4B); in Group 7, lyophilized allograft 35 with shaved articular surface and OP-1, and muscle flap 36 treated with OP-1 were implanted (see FIG. 4C); and, in Group 8, lyophilized allograft 37 with a non-shaved articular surface and OP-1, and muscle flap 36 treated with OP-1 were implanted (see FIG. 4D). Grafts in Groups 5–8 were harvested at 6 months after surgery.

Based upon pre-harvest imaging studies, the results collected by 3 months post-operative are consistent with the above-described results collected at 5 weeks. Intact allografts treated with OP-1 (Group 8) regenerated a live cartilaginous articular surface by 3 weeks when evaluated using MRI. This articular cap is still present and even better developed at 3 months. Without OP-1 treatment of the allograft, (Group 6) there was negligible cartilage regeneration relative to the OP-1 treated groups.

Similarly, Group 8 rabbits (allograft+OP1, non-shaved) regained near normal range of motion (greater than 80%) in the reconstructed joint. Group 7 rabbits (allograft+OP1, shaved) achieved only 50% range of motion, and Groups 5 and 6 (no OP1) achieved less than 30%.

As determined by histology, the devices of the invention were competent to induce and maintain both bone and articular cartilage formation in the appropriate context to one another in a long term study(greater than 6 months). Specifically, the rabbits of Group 8, demonstrated articular cartilage formation on the surface of bone, as evidenced morphologically by the presence of resting, central and deeper zone chondrocytes. By contrast, in groups treated only with muscle flap, (Group 5 and 6) muscle was replaced with scar tissue. In the groups treated with shaved bone matrices, no significant cartilage regeneration was identified, demonstrating the requirement for cartilage-specific residues in articular cartilage formation in a non-vascularized milieu.

In both the short term and long term study, mechanically and functionally viable synovial joints resulted from the reconstructed hemijoints treated with osteogenic protein, as evidenced by morphology and biochemistry. In addition, new tissue formed, including articular cartilage, corresponding in shape, kind and structural relationship to the residues in the devitalized tissue which formed the matrix of the device. Collectively, these examples demonstrate that a device comprising osteogenic protein and an off-the-shelf, non-viable lyophilized, devitalized matrix can be transformed into a viable, mechanically and structurally functional replacement body part structure comprising plural distinct newly formed tissues which assume the shape and function of the original tissue. The device can restore normal function to a destroyed body part, including a destroyed skeletal joint, restoring mechanically and functionally viable plural distinct tissues, including bone and bone marrow, articular cartilage, ligament, tendon, synovial capsule and synovial membrane tissue. Moreover, these tissues are restored under substantially physiological conditions including, for example, from responding cells present in a synovial environment, and without exposure to a vascularized muscle flap.

A device comprising osteogenic protein-treated matrices, including lyophilized allografts or xenografts as disclosed herein can lead to the format ion of a new, mechanically, structurally and functionally viable replacement tissue, and to replacement body parts comprising plural distinct tissues, populated by the host cells, and without any of the limitations of prosthetic materials.

Those skilled in the art will know, or be able to ascertain using no more than routine experimentation, many equivalents to the specific embodiments of the invention described herein. These and all other equivalents are intended to be encompassed by the following claims.

What is claimed is:

1. A device for repair of a skeletal joint defect in a mammal which serves as a template to form in vivo a functional replacement skeletal joint which is long term mechanically and functionally viable, comprising plural distinct tissues, the device comprising:

a) a biocompatible, biodegradable matrix defining a unitary intact structure allowing the attachment of infiltrating cells, and comprising plural distinct tissues derived from a proximal or distal hemi-joint including at least one non-mineralized tissue of a joint and including bone underlying the articular surface wherein said underlying bone extends through the margin of articular cartilage into the supporting cancellous bone of said proximal or distal hemi-joint, and, having dimensions and shape conforming to the skeletal joint to be repaired; and disposed on the surface of said matrix, b) an exogenous osteogenic protein deposited on the matrix surface in an amount sufficient to induce formation of new said plural distinct tissues having dimensions and shape which conform to the skeletal joint to be repaired, thereby to permit regeneration of a functional replacement skeletal joint comprising plural distinct tissues.

2. The device of claim 1 wherein said matrix comprises devitalized tissue from a mammalian donor.

3. The device of claim 1 wherein the matrix comprises dehydrated mammalian tissue.

4. The device of claim 1 wherein said non-mineralized tissue is selected from the group consisting of articular cartilage, ligament, tendon, joint capsule, menisci, intervertebral discs, and synovial membrane tissue.

5. The device of claim 1 wherein said skeletal joint defines a synovial or articulating joint.

6. The device of claim 1 wherein said matrix defines a devitalized skeletal joint structure.

7. A device for implantation in a mammal which serves as a template for forming in vivo articular cartilage replacement tissue which is long term mechanically and functionally viable, in a skeletal, joint the device comprising:
exogenous osteogenic protein disposed on the surface of a biocompatible, bioresorbable matrix,
said matrix comprising plural distinct tissues derived from a proximal or distal hemi-joint including articular cartilage, said tissues defining a unitary structure which allows the attachment of infiltrating thereby to permit regeneration of said articular cartilage in a skeletal joint.

8. A device for implantation in a mammal which serves as a template for forming in vivo replacement of non-mineralized tissue which is long term mechanically and functionally viable in a skeletal joint, the device comprising:
exogenous osteogenic protein disposed on the surface of a biocompatible, bioresorbable matrix,
said matrix comprising plural distinct tissues derived from a proximal or distal hemi-joint including at least one non-mineralized tissue corresponding in kind to said tissue to be replaced said matrix defining a unitary structure which allows the attachment of infiltrating cells thereby to permit regeneration of non-mineralized tissue in a skeletal joint.

9. The device of claim 8 wherein said non-mineralized tissue is an avascular tissue.

10. The device of claim 8 wherein said non-mineralized tissue is selected from the group consisting of articular cartilage, ligament, tendon, synovial membrane, menisci, intervertebral discs, and joint capsule tissue.

11. The device of claim 7 or 8 wherein said matrix comprises devitalized allogenic or xenogenic tissue.

12. The device of claim 1, 7 or 8 further comprising a material selected from the group consisting of: collagen, polymers comprising monomers of lactic acid, glycolic acid, butyric acid and combinations thereof, hydroxyapatite, tricalcium phosphate, and mixtures thereof.

13. The device of claim 12 further comprising a material suitable for binding particulate matter to form a moldable solid.

14. The device of claim 1, 7, or 8, wherein said exogenous osteogenic protein comprises homodimers or heterodimers of OP-1, OP-2, BMP2, BMP3, BMP4, BMP5, BMP6, OPX, or phylogenetic and biosynthetic variants thereof.

15. The device of claim 1, 7 or 8 wherein said skeletal joint defines a portion of a synovial or articulating joint.

16. The device of claim 1, 7 or 8 wherein said matrix is devitalized.

17. The device of claim 1, 7 or 8 wherein said exogenous osteogenic protein is OP-1 or a related osteogenic protein.

18. The device of claim 1, 7 or 8 wherein said exogenous osteogenic protein is OP-1.

19. A method for inducing in a mammal the formation of a replacement skeletal joint which is long term mechanically and functionally viable, said method comprising the steps of:
a) providing a device which serves as a template comprising exogenous osteogenic protein disposed on the surface of a bioresorbable, biocompatible matrix, said matrix
defining a single unitary intact structure allowing the attachment of infiltrating cells, and,
comprising plural distinct tissues from a proximal or distal hemi-joint including at least one non-mineralized tissue of a joint and including bone underlying the articular surface wherein said underlying bone extends through the margin of articular cartilage into the supporting cancellous bone of said proximal or distal hemi-joint, and,
having dimensions and shape which conform to the skeletal joint to be replaced; and
b) implanting said device at a locus in a mammal, thereby to induce formation of a functional replacement skeletal joint comprising plural distinct tissues.

20. The method of claim 19 wherein at least one non-mineralized tissue is selected from the group consisting of articular cartilage, ligament, tendon, joint capsule, menisci, intervertebral discs, and synovial membrane tissue.

21. The method of claim 19 wherein said matrix comprises devitalized allogenic or xenogenic tissue.

22. The method of claim 19 wherein one of said plural distinct tissues is an avascular tissue.

23. A method for repairing in vivo in a mammal an articular cartilage defect the method comprising the step of:
providing to said defect in a mammal a device which serves as a template comprising an exogenous osteogenic protein disposed on the surface of a biocompatible, bioresorbable matrix, said matrix comprising plural distinct tissues derived from a proximal or distal hemi-joint articular cartilage, said tissues defining a structure which allows the attachment of infiltrating cells thereby to permit regeneration of said articular cartilage in a skeletal joint which is long term mechanically and functionally viable.

24. The method of claim 18 or 23 wherein said osteogenic protein comprises homodimers or heterodimers of OP-1, BMP2, BMP3, BMP4, BMP5, BMP6, OPX or phylogenetic and biosynthetic variants thereof.

25. The method of claim 19 or 23 wherein said exogenous osteogenic protein is OP-1 or a related protein.

26. The method of claim 19 or 23 wherein said exogenous osteogenic protein is OP-1.

27. The method of claim 23 wherein said defect occurs in a synovial cavity.

28. The method of claim 23 wherein said matrix is derived from allogenic or xenogenic articular cartilage.

29. The method of claim 23 wherein said device further comprises collagen, polymers comprising lactic acid, butyric glycolic acid or mixtures thereof; hydroxyapatite and combinations thereof.

30. A method for repairing in vivo in a mammal a non-mineralized tissue defect in a skeletal joint, the method comprising the step of:
providing to said defect a device which serves as a template comprising exogenous osteogenic protein disposed on the surface of a biocompatible, bioresorbable matrix, said matrix comprising plural distinct tissues derived from a proximal or distal hemi-joint including at least one non-mineralized tissue corresponding in kind to said tissue to be replaced, said matrix defining a unitary structure which allows the attachment of infiltrating cells thereby to permit regeneration of said non-mineralized tissue in a skeletal joint which is long term mechanically and functionally viable.

\* \* \* \* \*

UNITED STATES PATENT AND TRADEMARK OFFICE
CERTIFICATE OF CORRECTION

PATENT NO.    : 6,110,482                                        Page 1 of 1
DATED         : August 29, 2000
INVENTOR(S)   : Khouri et al.

It is certified that error appears in the above-identified patent and that said Letters Patent is hereby corrected as shown below:

<u>Title page,</u>
Item [56], References Cited, under U.S. PATENT DOCUMENTS, after "Pat. No. 5,492697, insert: -- 5,652,118   7/1997   Ozkaynak et al.        35/69.1 --
Under FOREIGN PATENT DOCUMENTS, after "WO 94/26893," insert:
-- WO 95/0131 --
Under OTHER PUBLICATIONS, before "Okada et al.," insert:
-- Asch et al. (1998) "Transplantation ... of the Patella in the Rat," translation of *Revue du Rheumatisme*, 55(1), pp. 7-14

Thomson et al. (1975) "An Improved Technique for Allogenic Hip Joint Transplantations," *Clinical Orthopaedics and Related Research*, 106:86-93 --

Signed and Sealed this

Sixth Day of August, 2002

*Attest:*

JAMES E. ROGAN
*Attesting Officer*          *Director of the United States Patent and Trademark Office*

UNITED STATES PATENT AND TRADEMARK OFFICE
CERTIFICATE OF CORRECTION

PATENT NO. : 6,110,482
DATED : August 29, 2000
INVENTOR(S) : Khouri et al.

It is certified that error appears in the above-identified patent and that said Letters Patent is hereby corrected as shown below:

<u>Title page,</u>
Item [56], References Cited, under U.S. PATENT DOCUMENTS, after "Pat. No. 5,492697, insert: -- 5,652,118  7/1997  Ozkaynak et al.  35/69.1 --
Under FOREIGN PATENT DOCUMENTS, after "WO 94/26893," insert:
-- WO 95/01131 --
Under OTHER PUBLICATIONS, before "Okada et al.," insert:
-- Asch et al. (1998) "Transplantation … of the Patella in the Rat," translation of *Revue du Rheumatisme*, 55(1), pp. 7-14

Thomson et al. (1975) "An Improved Technique for Allogenic Hip Joint Transplantations," *Clinical Orthopaedics and Related Research*, 106:86-93 --

This certificate supersedes Certificate of Correction issued August 6, 2002.

Signed and Sealed this

Seventeenth Day of June, 2003

JAMES E. ROGAN
*Director of the United States Patent and Trademark Office*